(12) United States Patent
Tsai (10) Patent No.: US 6,409,704 B1
(45) Date of Patent: Jun. 25, 2002

(54) RETRACTABLE SAFETY SYRINGE

(76) Inventor: Hsi-Chin Tsai, Shulin (TW)

( * ) Notice: Subject to any disclaimer, the term of this patent is extended or adjusted under 35 U.S.C. 154(b) by 0 days.

(21) Appl. No.: 09/988,916

(22) Filed: Nov. 19, 2001

(51) Int. Cl.[7] .............................. A61M 5/00; A61M 5/32
(52) U.S. Cl. ....................................... 604/110; 604/195
(58) Field of Search ................................ 604/110, 195, 604/197, 198, 218; 128/919

(56) References Cited

U.S. PATENT DOCUMENTS

| | | | | |
|---|---|---|---|---|
| 5,171,300 A | * | 12/1992 | Blake et al. ................ | 604/110 |
| 5,215,533 A | * | 6/1993 | Robb .......................... | 604/195 |
| 5,328,484 A | * | 7/1994 | Somers et al. .............. | 604/110 |

* cited by examiner

Primary Examiner—Michael J. Hayes
(74) Attorney, Agent, or Firm—Hedman & Costigan, P.C.

(57) ABSTRACT

A retractable safety syringe consists of a syringe barrel, a needle mount, a plunger rod and a needle. The needle mount is integrated with an outer hub and an inner hub having a plurality equal-spaced spring clamps formed at a lower end thereof. The plunger rod has a plunger formed with a plunger crown with a cone-shaped tip end portion formed on a top thereof and a neck portion formed between the tip end portion and the plunger crown. When the plunger rod is fully extended into the syringe barrel, the tip end portion is inserted into the lower end of the needle mount and the neck portion is clamped by the spring clamps. The needle is able to be retracted into the syringe barrel after finishing an injection procedure.

7 Claims, 5 Drawing Sheets

RETRACTABLE SAFETY SYRINGE

BACKGROUND OF THE INVENTION

1. Field of the Invention

The present invention relates to a retractable safety syringe having a simple structure, which allows ready assembly and safe use and disposal of the syringe so as to prohibit re-use of the syringe.

2. Description of Related Art

Hypodermic syringes are used to deliver medicine fluids in a safe and hygienic manner to patients. However it is found that for various reasons some syringes are re-used and this can result in transfer of diseases to the people injected with the re-used syringes. Thus there are various single-use-only safety syringes designed and produced to enable users to readily operate and dispose the syringes after finishing an injection procedure. The conventional safety syringe comprises a retractable needle which allows the needle to be connected with the plunger rod and retracted into the syringe barrel after finishing of the injection procedure.

However, the conventional safety retractable syringes still have some disadvantages which are as follow.

1. Most of the conventional retractable safety syringes are difficult to use due to their complex structure and multi-components configuration. The complex structure of the conventional syringe also decreases the efficiency of manufacturing and increases the manufacturing costs.

2. Some conventional syringes still have medicine residue in the syringe barrel when the plunger rod is fully extended into the syringe barrel, so that the needle is not properly connected with the plunger rod, which results in that the needle can not be retracted into the syringe barrel.

3. Also because of the complicated structure of some conventional syringes, the medicine fluid is not able to directly flow from the barrel towards the needle of the syringe, whereby some air bubbles occur in the medicine fluid. These bubbles can be harmful to a patient who may already be in poor health.

Therefore, it is an objective of the invention to provide an improved single-use-only and disposable retractable safety syringe to mitigate and/or obviate the aforementioned problems.

SUMMARY OF THE INVENTION

The main object of the present invention is to provide an improved retractable safety syringe comprising a needle mount fixed at an upper end of a syringe barrel, a plunger rod movably fitted in the syringe barrel and a needle fixed on the needle mount. Wherein the needle mount is integrated with an outer hub and an inner hub, the inner hub has a plurality equal-spaced spring clamps formed at a lower end of a fluid passage defined in a center thereof. The plunger rod consists of a rod and a plunger detachably connected at an upper end of the rod. The plunger is formed with a plunger crown having a cone-shaped tip end portion formed on a top thereof and a neck portion formed between the tip end portion and the plunger crown. When the plunger rod is fully fitted into the syringe barrel, the tip end portion is inserted into the fluid passage, and the neck portion is clamped by the spring clamps. The medicine fluid retained in the syringe barrel is able to flow over gaps between each two adjacent spring clamps, therefore the medicine fluid retention in the syringe is minimized, and the needle and needle mount are able to be retracted into the syringe barrel after finishing an injection procedure.

A further object of the invention is to provide an improved retractable safety syringe having a configuration feature that ensures ready assembly and use of the syringe.

Yet another object of the invention is to provide an improved retractable safety syringe having a simple structure, which enables the medicine fluid to directly flow in a substantially direct way from the syringe barrel over the fluid passage towards the needle.

Other objects, advantages and novel features of the invention will become more apparent from the following detailed description when taken in conjunction with the accompanying drawings.

DETAILED DESCRIPTION OF THE PREFERRED EMBODIMENT

Figure 1:
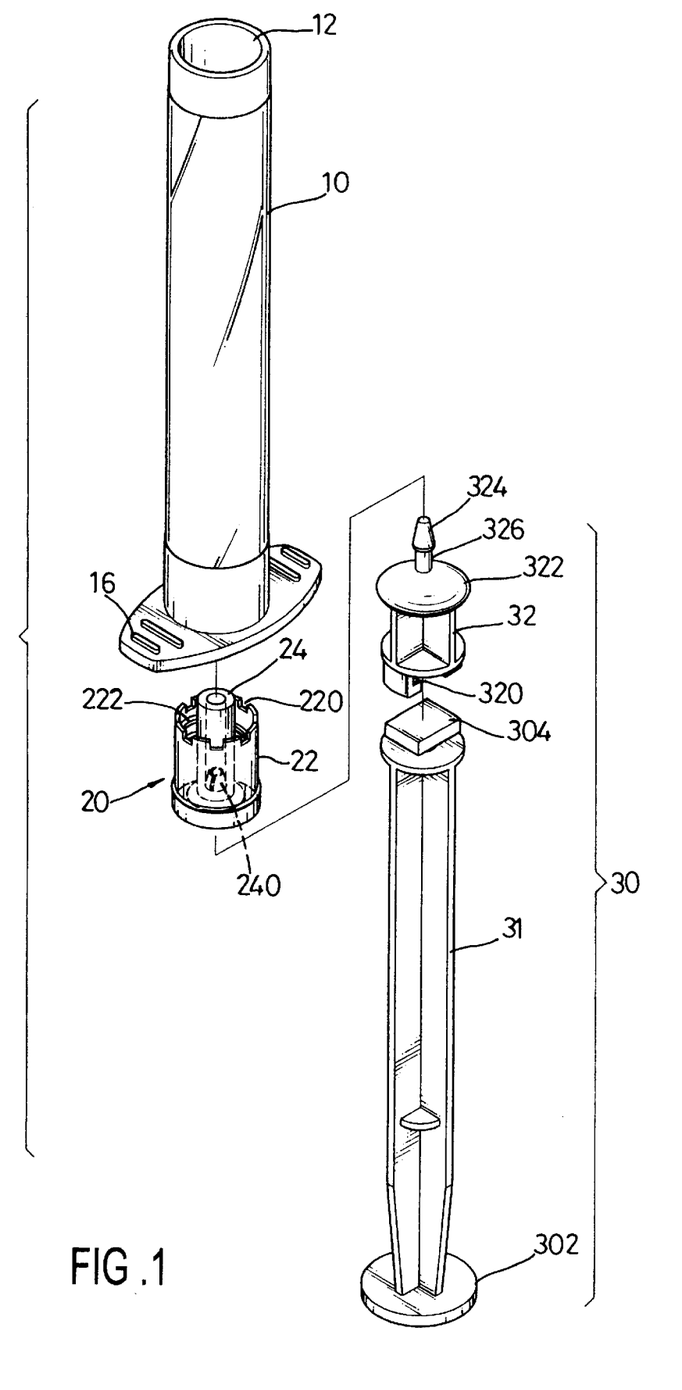
FIG. 1 is an exploded perspective view of a first embodiment of a retractable safety syringe in accordance with the invention.
Figure 2:
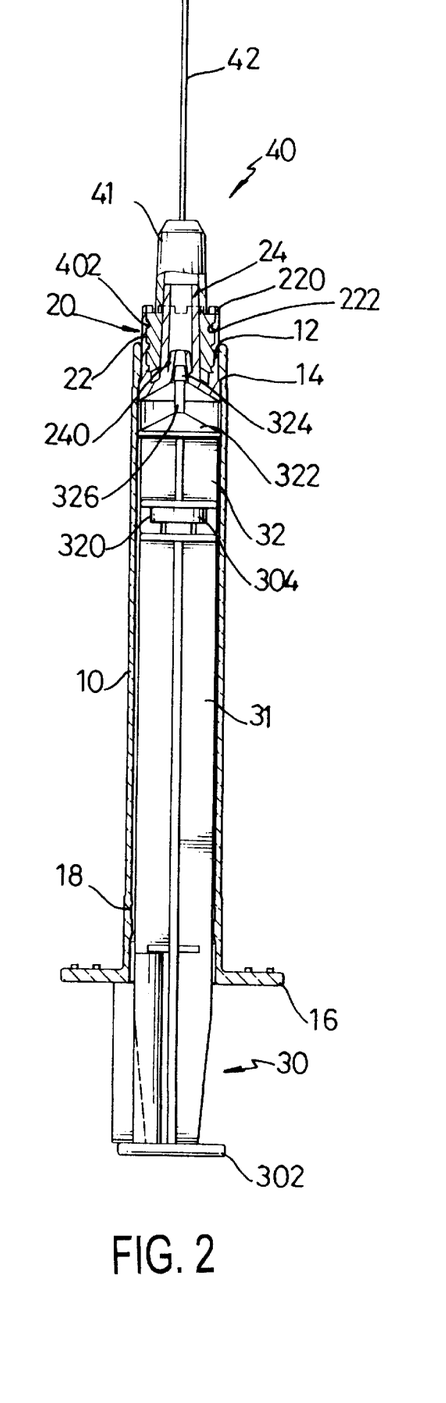
FIG. 2 is a cross sectional assembly view of the first embodiment of the retractable safety syringe in accordance with the invention.

With reference to FIGS. 1 and 2, a first embodiment of a retractable safety syringe in accordance with the invention is shown. The retractable safety syringe comprises a syringe barrel (10) for receiving of medicine fluid, a needle mount (20) securely assembled at an upper end of the syringe barrel (10), a plunger rod (30) movably fitted in the syringe barrel (10), and a needle (40) fixed on the needle mount (20).

The syringe barrel (10) is a tubular member having a fixing hole (12) defined in an upper end thereof, a retaining edge (14) integrated around an internal surface near the upper end thereof, a thumb press (16) formed at a lower end thereof, and an annular retaining groove (18) defined around the internal surface near the lower end thereof The needle mount (20) is assembled in the fixing hole (12) of the syringe barrel (10) and limited by the retaining edge (14). The needle mount (20) has an outer hub (22) and an inner hub (24) integrally formed therewith, wherein the outer hub (22) has an upper end thereof defined with a plurality of notches (220), and an internal surface thereof formed with a female thread (222). The inner hub (24) is defined with a fluid passage in a center thereof and further has a plurality of equal-spaced spring clamps (240) integrated at a lower end of the fluid passage and extending in an inclined way toward an upper end of the fluid passage.

The plunger rod (30) consists of a rod (31) and a plunger (32) detachably connected at an upper end of the rod (31). The rod (31) has a joint block (304) formed at an upper end thereof, and a press plate (302) integrated at a lower end thereof. The plunger (32) has a joint groove (320) defined in a lower end thereof to receive the joint block (304) of the rod (31) detachably fitted therein, and a plunger crown (322) formed at an upper end thereof. The plunger (32) further has a cone-shaped tip end portion (324) formed on a top of the plunger crown (322), and a neck portion (326) formed between the tip end portion (324) and the plunger crown (322).

The needle (40) includes a connecting portion (41) and a needle cannula (42). The connecting portion (41) of the needle (40) has a male thread (402) formed therearound corresponding to the female thread (222) formed around the internal surface of the outer hub (22) of the needle mount (20), whereby the needle (40) is threadingly engaged on the needle mount (20). The plurality of notches (220) formed around the outer hub (22) is intended to facilitate positioning of the needle mount (20) to be properly positioned in a fixture of an assembly line for production of the syringe.

Figure 3:
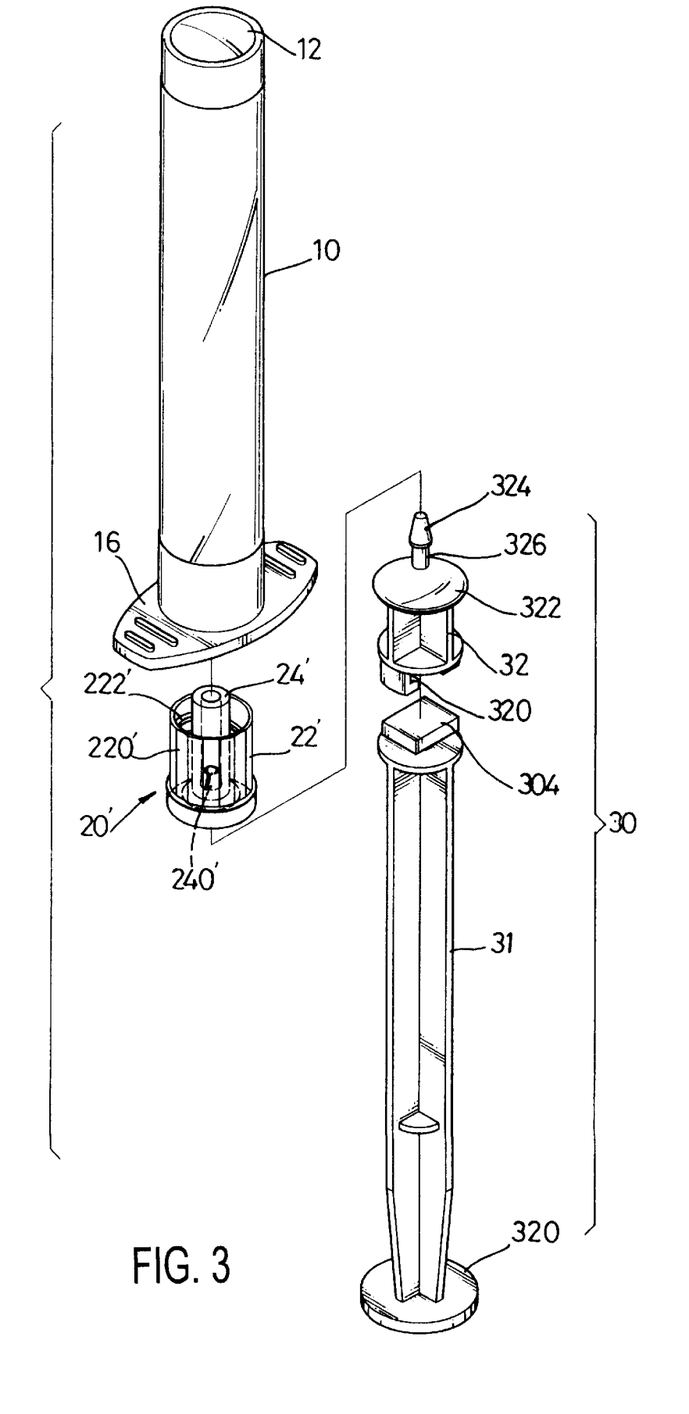
FIG. 3 is an exploded perspective view of a second embodiment of the retractable safety syringe in accordance with the invention.
Figure 4:
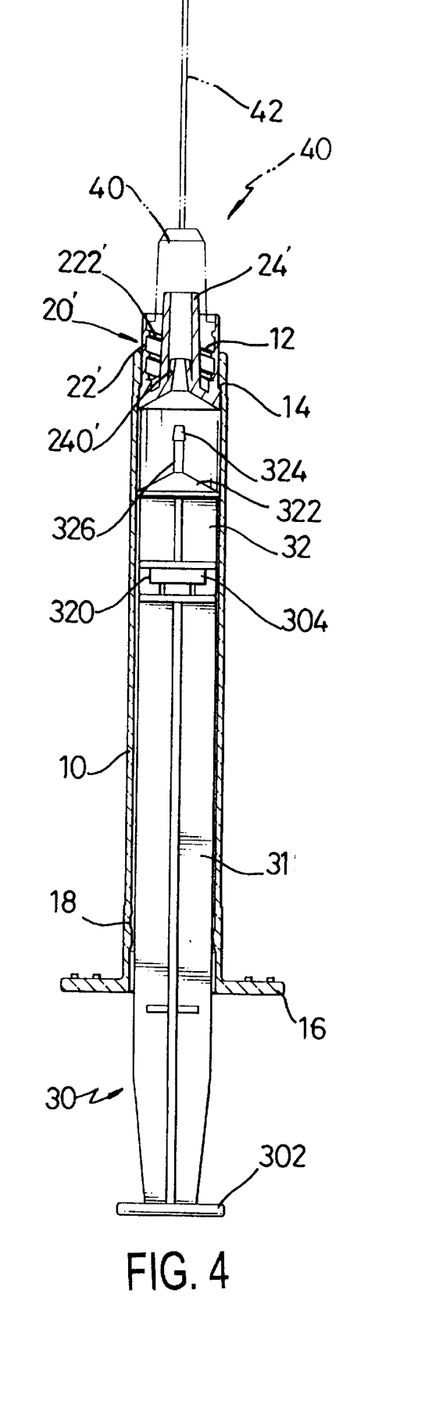
FIG. 4 is a cross sectional assembly view of the second embodiment of the retractable safety syringe in accordance with the invention.

As shown in FIGS. 3 and 4, a second practicable embodiment of the invention has a structure basically in the same principal as the first embodiment of the retractable safety syringe. In the second embodiment, instead of the plurality of notches (220), the outer hub (22) of the needle mount (20) of the syringe has a plurality of chamfers (220') formed around an external surface thereof. The plurality of chamfers (220') is also intended to facilitate positioning of the needle mount (20) in the fixture of the assembly line.

Figure 5:
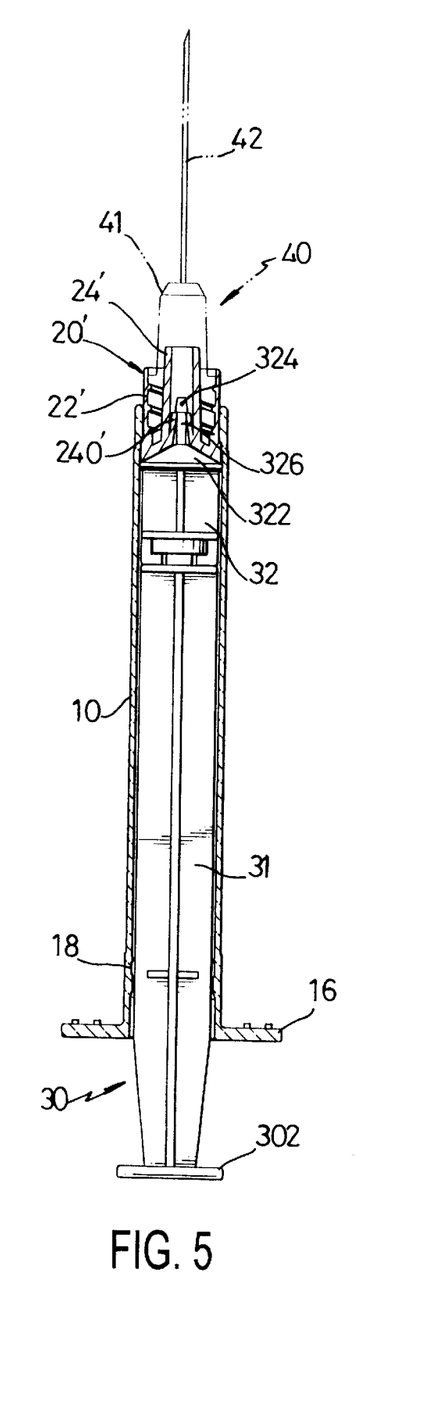
FIGS. 5, 6 and 7 are schematic operation views of the retractable safety syringe in accordance with the invention.
Figure 6:
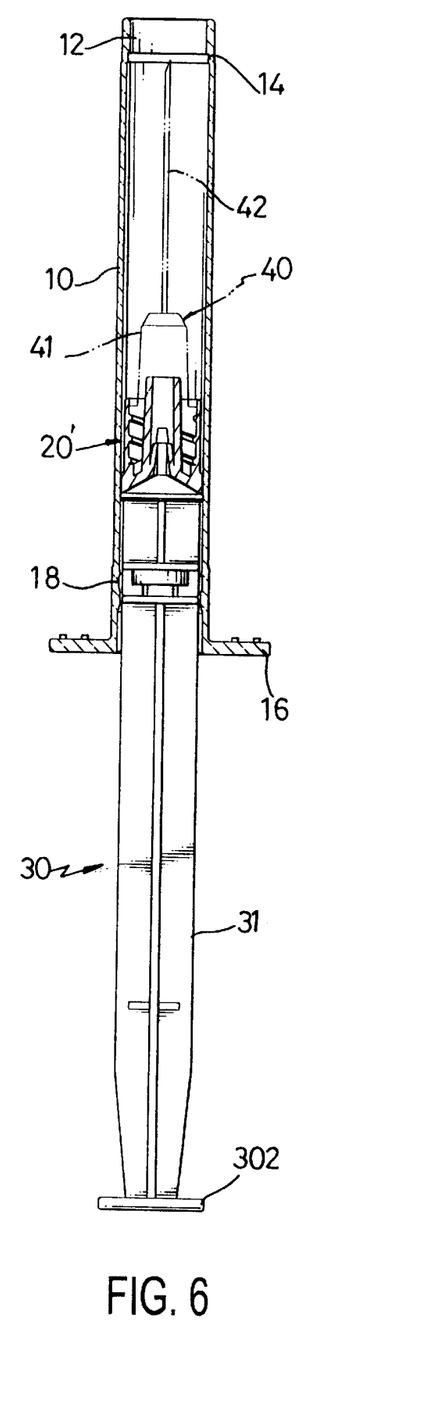
Figure 7:
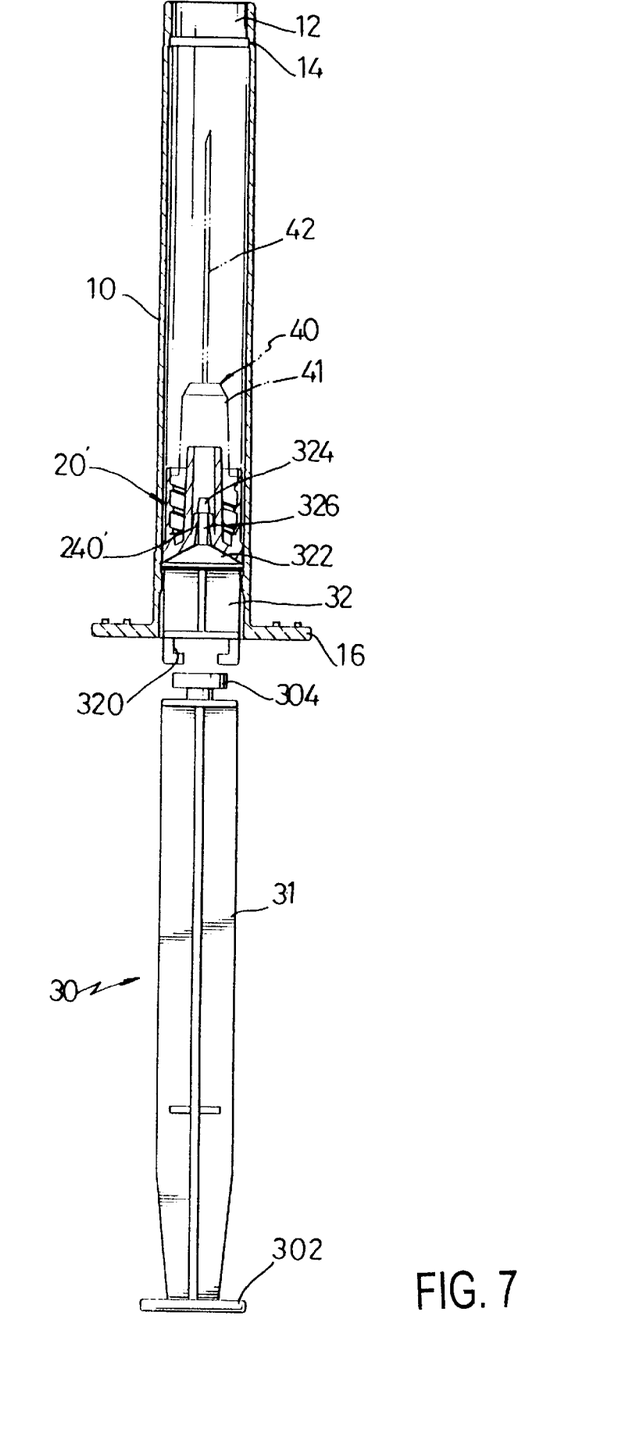

Now with reference to FIGS. 5, 6 and 7, when the plunger rod (30) is moved from the lower end to the upper end of the syringe barrel (10), because the plunger crown (322) is particularly made of an elastic material, a peripheral edge of the plunger crown (322) abuts tightly against the internal surface of the syringe barrel (10). Then the cone-shaped tip end portion (324) is inserted into the fluid passage of the needle mount (20), because there are gaps defined between each two adjacent spring clamps (240), the medicine fluid retained in the syringe barrel (10) is still able to flow over the gaps of the spring clamps (240) towards the needle (40). The spring clamps (240) are first pressed outward by the cone-shaped tip end portion (324) to let the tip end portion (324) pass therethrough, and then spring inwardly to clamp the neck portion (326) so as to prohibit the tip end portion (324) from disengagement from the spring clamps (240). After finishing an injection procedure, a user can readily retract the plunger rod (30), then the needle (40) and the needle mount (20) are together retracted into the syringe barrel (10). When the plunger crown (322) moves up to the annular retaining groove (18), the peripheral edge of the plunger crown (322) is extended outwardly by its resilient force and limited in the retaining groove (18), so that the needle (40) and the plunger (32) are retained within the syringe barrel (10). Finally the rod (31) is detached from the plunger (32), and the used syringe of the invention can be safely disposed without fear of it being reused.

The retractable safety syringe of the invention has following advantages:

1. The structure of the retractable safety syringe is simple, whereby the medicine fluid in the syringe barrel (10) flows over the fluid passage of the needle mount (20) towards the needle (40) until the plunger (32) is fully extended into the syringe barrel (10) and the plunger crown (322) contacts the lower end of the needle mount (20), thus the medicine fluid retention in the syringe barrel (10) is minimized.

2. The medicine fluid in the safety syringe of the invention directly flows from the syringe barrel (40) over the fluid passage in a substantially direct way towards the needle (40), so that air bubbles are easily obviated.

3. Due to the simple structure of retractable safety syringe, the components of the retractable safety syringe are easily molded and assembled under low production cost and high production efficiency.

4. The structure of the present invention ensures that the tip end portion (324) is able to be inserted into the fluid passage of the inner hub (24) until the neck portion (326) is clamped by the spring clamps (240), so that the needle mount (20) is properly engaged with the plunger rod (30), and the user can easily withdraw the plunger rod (30) to retract the needle (40) in the syringe barrel (10). When the plunger crown (322) moves up to the annular retaining groove (18), the peripheral edge of the plunger crown (322) is extended outwardly by its resilient force and limited in the retaining groove (18), so that the needle (40) and the plunger (32) are retained within the syringe barrel (10), and the used syringe of the invention can be safely disposed without fear of it being reused.

5. Because the outer hub (22) of the needle mount is formed with a configuration feature to facilitate assembly of the needle (40), the safety of operation of the syringe is ensured.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A retractable safety syringe comprising:
   a syringe barrel (10) having a fixing hole (12) defined in an upper end thereof and a thumb press (16) formed at a lower end thereof;
   a needle mount (20) assembled in the fixing hole (12) and retained at the upper end of the syringe barrel (10), and integrally formed with an outer hub (22) and an inner hub (24), wherein the inner hub (24) has a fluid passage defined in a center thereof and a plurality of equal-spaced spring clamps (240) formed around a lower end of the fluid passage and extending in an inclined direction towards an upper end of the fluid passage;
   a plunger rod (30) consisting of a rod (31) and a plunger (32) detachably connected at an upper end of the rod (31), wherein the plunger (32) has a plunger crown (322), a cone-shaped tip end portion (324) formed on a top of the plunger crown (322), and a neck portion (326) formed between the tip end portion (324) and the plunger crown (322);
   a needle (40) including a connecting portion (41) and a needle cannula (42);
   whereby when the plunger rod (30) is completely extended into the syringe barrel (10), the tip end portion (324) is inserted into the fluid passage of the needle mount (20), the neck portion (326) is clamped by the plurality of spring clamps (240), therefore, the medicine fluid is able to flow over gaps between each two adjacent spring clamps (240) toward the needle (40), and then the needle (40) and the needle mount (20) are connected with the plunger rod (30) and retractable with the plunger rod (30).

2. The retractable safety syringe as claimed in claim 1, wherein the outer hub (22) has a female thread (222) formed around an internal surface thereof, the connecting portion of the needle (40) is formed with a male thread corresponding to the female thread (222) of the outer hub (22).

3. The retractable safety syringe as claimed in claim 1, wherein the outer hub (22) has a plurality of notches (220) defined around an upper end thereof.

4. The retractable safety syringe as claimed in claim 1, wherein the outer hub (22) has a plurality of chamfers (220') formed around an external surface thereof.

5. The retractable safety syringe as claimed in claim 1, wherein the syringe barrel (10) has a retaining edge (14) integrated around an internal surface near the upper end thereof, the needle mount (20) is assembled in the fixing hole (12) and limited by the retaining edge (14).

6. The retractable safety syringe as claimed in claim 1, wherein the syringe barrel (10) has an annular retaining groove (18) defined around the internal surface near the lower end thereof, when the plunger rod (30) is retracted, a peripheral edge of the plunger crown (322) is limited by the retaining groove (18) within the syringe barrel (10).

7. The retractable safety syringe as claimed in claim 1, wherein the rod (31) has a joint block (304) formed at an upper end thereof, and the plunger (32) has a joint groove (320) defined in a lower end thereof to receive the joint block (304) detachably fitted therein.

\* \* \* \* \*

(12) EX PARTE REEXAMINATION CERTIFICATE (6180th)
United States Patent
Tsai (10) Number: US 6,409,704 C1
(45) Certificate Issued: Apr. 8, 2008

(54) RETRACTABLE SAFETY SYRINGE

(76) Inventor: Hsi-Chin Tsai, Shulin (TW)

Reexamination Request:
No. 90/008,002, Apr. 10, 2006

Reexamination Certificate for:
Patent No.: 6,409,704
Issued: Jun. 25, 2002
Appl. No.: 09/988,916
Filed: Nov. 19, 2001

(51) Int. Cl.
*A61M 5/32* (2006.01)

(52) U.S. Cl. .......................................... 604/110; 604/195
(58) Field of Classification Search ........................ None
See application file for complete search history.

(56) References Cited

U.S. PATENT DOCUMENTS 5,453,093 A    9/1995   Haining ...................... 604/110
5,899,887 A    5/1999   Liu ............................ 604/195

*Primary Examiner*—David O. Reip (57) ABSTRACT

A retractable safety syringe consists of a syringe barrel, a needle mount, a plunger rod and a needle. The needle mount is integrated with an outer hub and an inner hub having a plurality equal-spaced spring clamps formed at a lower end thereof. The plunger rod has a plunger formed with a plunger crown with a cone-shaped tip end portion formed on a top thereof and a neck portion formed between the tip end portion and the plunger crown. When the plunger rod is fully extended into the syringe barrel, the tip end portion is inserted into the lower end of the needle mount and the neck portion is clamped by the spring clamps. The needle is able to be retracted into the syringe barrel after finishing an injection procedure.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claim 2–7, dependent on an amended claim, are determined to be patentable.

1. A retractable safety syringe comprising:
   a syringe barrel (10) having a fixing hole (12) defined in an upper end thereof and a thumb press (16) formed at a lower end thereof;
   a needle mount (20) assembled in the fixing hole (12) and retained at the upper end of the syringe barrel (10), and integrally formed with an outer hub (22) and an inner hub (24) *concentrically surrounded by the outer hub* (*22*), wherein the inner hub (24) has a fluid passage defined in a center thereof and a plurality of equal-spaced spring clamps (240) formed around a lower end of the fluid passage and extending in an inclined direction towards an upper end of the fluid passage;
   a plunger rod (30) consisting of a rod (31) and a plunger (32) detachably connected at an upper end of the rod (31), wherein the plunger (32) has a plunger crown (322), a cone-shaped tip end portion (324) formed on a top of the plunger crown (322), and a neck portion (326) formed between the tip end portion (324) and the plunger crown (322);
   a needle (40) including a connecting portion (41) and a needle cannula (42);
   whereby when the plunger rod (30) is completely extended into the syringe barrel (10), the tip end portion (324) is inserted into the fluid passage of the needle mount (20), the neck portion (326) is clamped by the plurality of spring clamps (240), therefore, the medicine fluid is able to flow over gaps between each two adjacent spring clamps (240) toward the needle (40), and then the needle (40) and the needle mount (20) are connected with the plunger rod (30) and retractable with the plunger rod (30).

* * * * *